(12) United States Patent
Corsi et al.

(10) Patent No.: US 7,989,479 B2
(45) Date of Patent: Aug. 2, 2011

(54) USE OF A P38 KINASE INHIBITOR FOR TREATING PSYCHIATRIC DISORDERS

(75) Inventors: Mauro Corsi, Verona (IT); Isidore Faiferman, King of Prussia, PA (US); Emilio Merlo Pich, Verona (IT); Emiliangelo Ratti, Verona (IT); Paul Bryan Wren, Verona (IT)

(73) Assignee: GlaxoSmithKline LLC, Philadelphia, PA (US)

( * ) Notice: Subject to any disclaimer, the term of this patent is extended or adjusted under 35 U.S.C. 154(b) by 119 days.

(21) Appl. No.: 12/305,045

(22) PCT Filed: Jun. 13, 2007

(86) PCT No.: PCT/EP2007/055858
§ 371 (c)(1),
(2), (4) Date: Sep. 25, 2009

(87) PCT Pub. No.: WO2007/144390
PCT Pub. Date: Dec. 21, 2007

(65) Prior Publication Data
US 2010/0016377 A1    Jan. 21, 2010

(30) Foreign Application Priority Data
Jun. 16, 2006  (GB) .................................. 0612026.5

(51) Int. Cl.
*A61K 31/44*  (2006.01)
(52) U.S. Cl. ...................................................... 514/355
(58) Field of Classification Search .................. 514/355
See application file for complete search history.

(56) References Cited

U.S. PATENT DOCUMENTS

| | | | |
|---|---|---|---|
| 7,125,898 B2 | 10/2006 | Aston et al. | 546/268.1 |
| 7,151,118 B2 | 12/2006 | Angell et al. | 514/63 |
| 7,166,623 B2 | 1/2007 | Angell et al. | 514/227.8 |
| 7,183,297 B2 | 2/2007 | Angell et al. | 514/217.12 |
| 7,208,629 B2 | 4/2007 | Angell et al. | 544/60 |
| 7,271,289 B2 | 9/2007 | Aston | |
| 7,309,800 B2 | 12/2007 | Angell et al. | |
| 7,384,963 B2 | 6/2008 | Angell et al. | 546/228 |
| 7,396,843 B2 | 7/2008 | Angell et al. | 514/217.12 |
| 7,425,555 B2 | 9/2008 | Angell et al. | |
| 7,432,289 B2 | 10/2008 | Angell et al. | 514/63 |
| 2005/0065195 A1 | 3/2005 | Angell et al. | 514/364 |
| 2006/0122221 A1 | 6/2006 | Angell et al. | |
| 2006/0264479 A1 | 11/2006 | Aston et al. | 546/268.1 |
| 2006/0276516 A1 | 12/2006 | Aston et al. | 546/268.1 |
| 2007/0054942 A1 | 3/2007 | Patel et al. | |
| 2007/0105850 A1 | 5/2007 | Aston | |
| 2007/0112046 A1 | 5/2007 | Angell et al. | |
| 2007/0129354 A1 | 6/2007 | Aston et al. | |
| 2007/0142372 A1 | 6/2007 | Campos et al. | |
| 2007/0142476 A1 | 6/2007 | Angell et al. | |
| 2007/0161684 A1 | 7/2007 | Walker | |
| 2008/0051416 A1 | 2/2008 | Boehm et al. | |
| 2008/0214623 A1 | 9/2008 | Chandi et al. | |

FOREIGN PATENT DOCUMENTS

| | | |
|---|---|---|
| WO | WO 03/068747 | 8/2003 |
| WO | WO 03/097062 | 11/2003 |
| WO | WO 2007/147103 | 12/2007 |
| WO | WO 2007/147104 | 12/2007 |
| WO | WO 2007/147109 | 12/2007 |

OTHER PUBLICATIONS

The Merck Index, Merck & Co., 13th Edition, Whitehouse Station, NJ p. 12 (2001).

*Primary Examiner* — Jennifer M Kim
(74) *Attorney, Agent, or Firm* — James P. Riek

(57) ABSTRACT

The use of 6-(S-Cyclopropylcarbamoyl-S-fluoro-2-methyl-phenyl)-N-(2,2-dimethylproyl)-nicotinamide, which is known in the art as a p38 kinase inhibitor in the treatment or prophylaxis of one or more psychiatric disorders.

6 Claims, No Drawings

USE OF A P38 KINASE INHIBITOR FOR TREATING PSYCHIATRIC DISORDERS

This application is a §371 of International Application No. PCT/EP07/55858, filed 13 Jun. 2007, which claims the priority of GB Application No. 0612026.5, filed 16 Jun. 2006, which are incorporated herein in their entirety.

This invention relates to a new pharmaceutical use of a compound which is known in the art as a p38 kinase inhibitor. More specifically this invention relates to the use of a nicotinamide derivative in the treatment or prophylaxis of psychiatric disorders.

P38 is a serine kinase that plays a central role in inflammation (Schieven G L, 2005. Curr. Top. Med. Chem. 5: 921-928) and hence is considered a molecular target for classical inflammatory diseases (Kumar et al., 2003. Nat. Rev. Drug Disc. 2: 717-726, Saklatuala et al., 2004. Curr Opin. Pharmacol. 4: 372-377.). Small molecule synthetic inhibitors have been designed in an attempt to treat pain, multiple myeloma and rheumatoid arthritis (Peiffer et al., 2006. Curr. Top. Med. Chem. 6: 113-149). However their utility could be extended to explore other conditions, particularly in Neuropsychiatry, where evidences of inflammatory mechanisms are apparent in depression, anxiety, schizophrenia and sleep disorders.

Pro-inflammatory cytokines, such as IL-1, IL-6 & TNF- are commonly elevated in the plasma of depressed patients (Elenkov I J et al., 2005. Neuroimmunomod. 12: 255-269, Hayley S et al., 2005. Neurosci. 135: 659-678, Raison C L et al., 2006. Trends in Immuno. 27: 24-31) and bipolar patients in both the depressed and mania phases (O'Brien S M. et al., 2006. J. Affective Disorders. 90: 263-267.). In animals, systemic injection of such pro-inflammatory cytokines result in a sickness like behaviour that can mimic some of the symptoms observed in depression in man which can be reversed by antidepressant drugs (Simen B B et al., 2006. Biol Psychiatry. 59: 775-785). These cytokines can increase the activity of monoamine transporters, known molecular targets of antidepressants, through a P38 dependent mechanism (Zhu et al., 2006. Neuropsychopharmacol. ahead of print, Prasad H C et al., 2005. PNAS. 102: 11545-11550). P38 inhibitors, or mechanisms that have the potential to decrease pro-inflammatory mediators can stabilise monoamine transporter activity and could therefore be antidepressant drugs. The soluble TNF-receptor, etanercept, which sequesters TNF-signalling, has demonstrated efficacy in alleviating clinical symptoms of psoriasis on fatigue and symptoms of depression associated with the condition (Tyring S. et al., 2006. Lancet. 367: 29-35.). Like depression, anxiety, commonly apparent under stressful conditions is also regulated by the immune system and pro-inflammatory cytokines (Holden R J & Pakula I S. 1999. Med. Hypotheses. 52: 155-162, Pitsavos C et al., 2006. Atherosclerosis. 185: 320-326). P38 inhibitors, by blocking the signalling of pro-inflammatory cytokines, therefore have the potential to treat multiple facets of depressive and anxiety disorders.

P38 inhibitor effects in depression may be assessed using randomised, double-blind, placebo-controlled studies compared to an active clinically effective comparator in patients with Major Depressive Disorders with elevated pro-inflammatory cytokine levels initially, enriched for loss of energy, pleasure, interest and with psychomotor retardation.

TNF-levels have also been reported to be elevated in animal models of schizophrenia and in schizophrenic patients. These elevated levels of pro-inflammatory cytokines can be normalized by antipsychotic drugs (Paterson G J et al., 2006. J. Psychopharmacol. ahead of print, Zhang X Y et al., 2005. Neuropsychopharmacol. 30: 1532-1538). Despite a lack of a genetic association between TNF and schizophrenia (Shirts B H et al., 2006. Schizophr. Res. 83: 7-13.), p38 inhibitors may still have utility in this psychiatric disorder when inflammatory signalling pathways are altered in the pathophysiology of the disease.

TNF- and IL-6 are also increased in normal subjects with sleep deprivation (Vgontzas A N et al. 2004 J Clin Endo Metab. 89: 2119-2126), in subjects with insomnia (Vgontzas A N et al 2002 Metabolism 7: 887-892.) and in subjects with sleep apnea (Hatipoglu U & Rubinstein I. 2003 Respiration 70: 665-671., Alberti A et al. 2003 J Sleep Res. 12: 305-311, Yokoe T et al. 2003. Circulation. 107: 1129-1134). Etanercept has also been used to demonstrate decreases in sleepiness in patients with sleep apnea (Vgontzas A N et al. 2004 J Clin Endocrinol Metab. 89: 4409-4413) suggesting that drugs that inhibit pro-inflammatory cytokines may return sleep architecture back to normal.

Patent application WO03/068747 (SmithKline Beecham Corporation) discloses a series of nicotinamide derivatives that are useful as p38 inhibitors. The compound 6-(5-Cyclopropylcarbamoyl-3-fluoro-2-methyl-phenyl)-N-(2,2-dimethylpropyl)-nicotinamide is specifically described therein.

According to the present invention there is provided the compound 6-(5-Cyclopropylcarbamoyl-3-fluoro-2-methylphenyl)-N-(2,2-dimethylpropyl)-nicotinamide

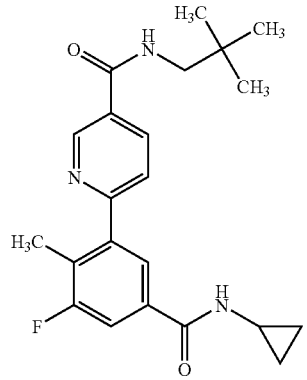

or a pharmaceutically acceptable salt or solvate in the manufacture of a medicament for use in the treatment or prophylaxis of one or more psychiatric disorder.

Salts of the compound of the present invention are also encompassed within the scope of the invention and may, for example, comprise acid addition salts resulting from reaction of an acid with a basic nitrogen atom present.

Salts encompassed within the term "pharmaceutically acceptable salts" refer to non-toxic salts of the compound of this invention. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate.

Preferably the compound 6-(5-Cyclopropylcarbamoyl-3-fluoro-2-methyl-phenyl)-N-(2,2-dimethylpropyl)-nicotinamide is in the form of a free base.

As used herein, the term "solvate" refers to a complex of variable stoichiometry formed by a solute (in this invention, the compound 6-(5-Cyclopropylcarbamoyl-3-fluoro-2-methyl-phenyl)-N-(2,2-dimethylpropyl)-nicotinamide or a pharmaceutically acceptable salt or solvate thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. All such solvates are included within the scope of the present invention.

The compound 6-(5-Cyclopropylcarbamoyl-3-fluoro-2-methyl-phenyl)-N-(2,2-dimethylpropyl)-nicotinamide or a pharmaceutically acceptable salt or solvate thereof may be prepared according to procedures described in patent application WO03/068747 (as example 36).

In one embodiment the psychiatric disorder is depression including Major Depressive Episode, Manic Episode, Mixed Episode and Hypomanic Episode; Depressive Disorders including Major Depressive Disorder, Dysthymic Disorder; Depressive Disorder Not Otherwise Specified; Bipolar Disorders including Bipolar I Disorder, Bipolar II Disorder (Recurrent Major Depressive Episodes with Hypomanic Episodes), Cyclothymic Disorder and Bipolar Disorder Not Otherwise Specified; Other Mood Disorders including Mood Disorder Due to a General Medical Condition which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified.

In a further embodiment the psychiatric disorder is Schizophrenia disorder including the subtypes Paranoid Type, Disorganised Type, Catatonic Type, Undifferentiated Type and Residual Type; Schizophrenic form Disorder; Schizoaffective Disorder including the subtypes Bipolar Type and Depressive Type; Delusional Disorder including the subtypes Erotomanic Type, Grandiose Type, Jealous Type, Persecutory Type, Somatic Type, Mixed Type and Unspecified Type; Brief Psychotic Disorder; Shared Psychotic Disorder; Psychotic Disorder Due to a General Medical Condition including the subtypes With Delusions and With Hallucinations; Substance-Induced Psychotic Disorder including the subtypes With Delusions and With Hallucinations; and Psychotic Disorder Not Otherwise Specified.

In a further embodiment the psychiatric disorder is an Anxiety disorder including Panic Attack; Panic Disorder including Panic Disorder without Agoraphobia and Panic Disorder with Agoraphobia; Agoraphobia; Agoraphobia Without History of Panic Disorder, Specific Phobia (formerly Simple Phobia) including the subtypes Animal Type, Natural Environment Type, Blood-Injection-Injury Type, Situational Type and Other Type), Social Phobia (Social Anxiety Disorder, Obsessive-Compulsive Disorder, Posttraumatic Stress Disorder, Acute Stress Disorder, Generalized Anxiety Disorder, Anxiety Disorder Due to a General Medical Condition, Substance-Induced Anxiety Disorder, Separation Anxiety Disorder, Adjustment Disorders with Anxiety and Anxiety Disorder Not Otherwise Specified.

In a further embodiment the psychiatric disorder is a Sleep disorder including primary sleep disorders such as Dyssomnias such as Primary Insomnia, Primary Hypersomnia, Narcolepsy, Breathing-Related Sleep Disorders, Circadian Rhythm Sleep Disorder and Dyssomnia Not Otherwise Specified; primary sleep disorders such as Parasomnias such as Nightmare Disorder, Sleep Terror Disorder, Sleepwalking Disorder and Parasomnia Not Otherwise Specified; Sleep Disorders Related to Another Mental Disorder such as Insomnia Related to Another Mental Disorder and Hypersomnia Related to Another Mental Disorder; Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

The invention provides, in a further aspect, 6-(5-Cyclopropylcarbamoyl-3-fluoro-2-methyl-phenyl)-N-(2,2-dimethylpropyl)-nicotinamide or a pharmaceutically acceptable salt or solvate thereof, for use in the treatment or prophylaxis of one or more psychiatric disorder, for example, depression, Schizophrenia, Anxiety and Sleep disorders of the types described above.

Whilst it is possible for the compound 6-(5-Cyclopropylcarbamoyl-3-fluoro-2-methyl-phenyl)-N-(2,2-dimethylpropyl)-nicotinamide or a pharmaceutically acceptable salt or solvate thereof to be administered as the new chemical it would typically be administered in the form of a pharmaceutical composition.

The compound may be formulated for administration in any suitable manner. They may, for example, be formulated for topical administration or administration by inhalation or, more preferably, for oral, transdermal or parenteral administration. The pharmaceutical composition may be in a form such that it can effect controlled release. A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), pills, powders, granules, elixirs, tinctures, emulsions, solutions, syrups or suspensions prepared by conventional means with acceptable excipients.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compound of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compound of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compound of the present invention may also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

The compound of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compound of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compound according to the invention can be conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The pharmaceutical compositions generally are administered in an amount effective for treatment or prophylaxis of a specific condition or conditions. Initial dosing in human is accompanied by clinical monitoring of symptoms, such symptoms for the selected condition. In general, the compositions are administered in an amount of active agent of at least about 100 µg/kg body weight. In most cases they will be administered in one or more doses in an amount not in excess of about 20 mg/kg body weight per day. Preferably, in most cases, dose is from about 100 µg/kg to about 5 mg/kg body weight, daily. For administration particularly to mammals, and particularly humans, it is expected that the daily dosage level of the active agent will be from 0.1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the age, weight and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

The present invention also provides for a method for treating one or more psychiatric disorder which comprises administering to a patient in need thereof the compound 6-(5-Cyclopropylcarbamoyl-3-fluoro-2-methyl-phenyl)-N-(2,2-dimethylpropyl)-nicotinamide or a pharmaceutically acceptable salt or solvate thereof.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms.

The compound of the present invention can be administered to any mammal in need thereof. Such mammals can include, for example, horses, cows, sheep, pigs, mice, dogs, cats, primates such as chimpanzees, gorillas, rhesus monkeys, and, most preferably, humans.

It will be appreciated that 6-(5-Cyclopropylcarbamoyl-3-fluoro-2-methyl-phenyl)-N-(2,2-dimethylpropyl)-nicotinamide may be employed alone or in combination with other therapeutic agents which are suitable for the treatment of the above mentioned psychiatric disorders.

6-(5-Cyclopropylcarbamoyl-3-fluoro-2-methyl-phenyl)-N-(2,2-dimethylpropyl)-nicotinamide and the other pharmaceutically active agent(s) may be administered together or separately and, when administered separately, this may occur separately or sequentially in any order. The amounts of 6-(5-Cyclopropylcarbamoyl-3-fluoro-2-methyl-phenyl)-N-(2,2-dimethylpropyl)-nicotinamide and the other pharmaceutically active agent(s) and the relative timings of administration will be selected in order to achieve the desired combined therapeutic effect.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

The invention provides, in a further aspect, a combination product comprising 6-(5-Cyclopropylcarbamoyl-3-fluoro-2-methyl-phenyl)-N-(2,2-dimethylpropyl)-nicotinamide, or a pharmaceutically acceptable salt or solvate thereof, together with an anti-inflammatory agent.

Suitable anti-inflammatory agents for use in combination with 6-(5-Cyclopropylcarbamoyl-3-fluoro-2-methyl-phenyl)-N-(2,2-dimethylpropyl)-nicotinamide, or a pharmaceutically acceptable salt or solvate thereof, include COX-2 inhibitors (such as Celebrex®, Vioxx®, or Prexige®), non-steroidal anti-inflammatory drugs (NSAID's) (such as sodium cromoglycate or nedocromil sodium), phosphodiesterase (PDE) inhibitors (such as theophylline, PDE4 inhibitors or mixed PDE3/PDE4 inhibitors), leukotriene antagonists, inhibitors of leukotriene synthesis (such as montelukast), iNOS inhibitors, tryptase and elastase inhibitors, beta-2 integrin antagonists, adenosine receptor agonists or antagonists (such as adenosine 2a agonists), cytokine antagonists (for example, chemokine antagonists, such as a CCR3 antagonist) or inhibitors of cytokine synthesis, 5-lipoxygenase inhibitors or a corticosteroid.

The invention provides, in a further aspect, a combination product comprising 6-(5-Cyclopropylcarbamoyl-3-fluoro-2-methyl-phenyl)-N-(2,2-dimethylpropyl)-nicotinamide, or a pharmaceutically acceptable salt or solvate thereof, together with one or more of the following agents to treat or prevent psychiatric disorders: i) anti-psychotics; ii) anti-depressants; iii) anxiolytics; and iv) mood stabilisers.

6-(5-Cyclopropylcarbamoyl-3-fluoro-2-methyl-phenyl)-N-(2,2-dimethylpropyl)-nicotinamide, or a pharmaceutically acceptable salt or solvate thereof, may be used in combination with antidepressants and/or antipsychotics to treat or prevent depression and mood disorders.

6-(5-Cyclopropylcarbamoyl-3-fluoro-2-methyl-phenyl)-N-(2,2-dimethylpropyl)-nicotinamide, or a pharmaceutically acceptable salt or solvate thereof, may be used in combination with one or more of the following agents to treat or prevent bipolar disease: i) mood stabilisers; ii) antipsychotics; and iii) antidepressants.

6-(5-Cyclopropylcarbamoyl-3-fluoro-2-methyl-phenyl)-N-(2,2-dimethylpropyl)-nicotinamide, or a pharmaceutically acceptable salt or solvate thereof, may be used in combination with anxiolytics and/or antidepressants to treat or prevent anxiety disorders.

6-(5-Cyclopropylcarbamoyl-3-fluoro-2-methyl-phenyl)-N-(2,2-dimethylpropyl)-nicotinamide, or a pharmaceutically acceptable salt or solvate thereof, may be used in combination with antipsychotics and/or antidepressants to treat or prevent schizophrenia.

6-(5-Cyclopropylcarbamoyl-3-fluoro-2-methyl-phenyl)-N-(2,2-dimethylpropyl)-nicotinamide, or a pharmaceutically acceptable salt or solvate thereof, may be used in combination with one or more of the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; and v) other sedative-hypnotics for example chloral hydrate and chlormethiazole.

Suitable antipsychotic drugs for use in combination with 6-(5-Cyclopropylcarbamoyl-3-fluoro-2-methyl-phenyl)-N-(2,2-dimethylpropyl)-nicotinamide, or a pharmaceutically acceptable salt or solvate thereof, include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Suitable anti-depressant drugs for use in combination with 6-(5-Cyclopropylcarbamoyl-3-fluoro-2-methyl-phenyl)-N-(2,2-dimethylpropyl)-nicotinamide, or a pharmaceutically acceptable salt or solvate thereof, include serotonin reuptake inhibitors (such as citalopram, escitalopram, fluoxetine, paroxetine, dapoxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Suitable mood stabiliser drugs for use in combination with 6-(5-Cyclopropylcarbamoyl-3-fluoro-2-methyl-phenyl)-N-(2,2-dimethylpropyl)-nicotinamide, or a pharmaceutically acceptable salt or solvate thereof, include lithium, sodium valproate/valproic acid/divalproex, carbamazepine, lamotrigine, gabapentin, topiramate and tiagabine.

Suitable anxiolytics for use in combination with 6-(5-Cyclopropylcarbamoyl-3-fluoro-2-methyl-phenyl)-N-(2,2-dimethylpropyl)-nicotinamide, or a pharmaceutically acceptable salt or solvate thereof, include benzodiazepines such as alprazolam and lorazepam.

6-(5-Cyclopropylcarbamoyl-3-fluoro-2-methyl-phenyl)-N-(2,2-dimethylpropyl)-nicotinamide, or a pharmaceutically acceptable salt or solvate thereof, may also be used in combination with one or more of: i) a melatonin receptor modulator; ii) an orexin antagonist; iii) a tachykinin receptor antagonist; iv) a CRF receptor antagonist; (v) a triple reuptake inhibitor; (vi) a sodium channel blocker; (vii) a D1, D2 or D3 receptor modulator; (viii) a serotonin receptor modulator; (ix) a vasopressin receptor modulator; (x) a glutamate receptor modulator; and (xi) a neuropeptideY receptor modulator, to treat or prevent psychiatric disorders.

Biological Evaluation

Study 1

Administration of lipopolysaccharide (LPS) to rats is known to produce not only robust measures of sickness behaviour (reduced locomotor activity, reduced intake of both food and water, decreased body weight & decreased social interest) but also large elevations of peripheral pro-inflammatory cytokines and HPA-axis markers that can mimic some of the symptoms and underlying pathobiology observed in major depressive disorder (Dunn et al., (2005). *Neurosci. Behav. Rev.*, 29, 891-909). Indeed the injection of cytokines into man produces such neuropsychiatric disturbances in non-major depressive disorder patients (Schiepers & Maes (2005). *Prog. Neuro-psychopharmacol. & Biol. Psych.*, 29, 201-217).

6-(5-Cyclopropylcarbamoyl-3-fluoro-2-methyl-phenyl)-N-(2,2-dimethylpropyl)-nicotinamide was administered (p.o.) 1 hour before the administration of LPS (125 ug/kg i.p.) and then behavioural assessments were performed 2 hours thereafter. A satelite group of animals were treated in the same way and blood samples taken for biomarker analysis. 6-(5-Cyclopropylcarbamoyl-3-fluoro-2-methyl-phenyl)-N-(2,2-dimethylpropyl)-nicotinamide significantly reversed the LPS induced sickness behaviour at 20 mg/kg p.o. again with >80% reduction in LPS induced elevations in TNF-a, IL-6, IL-10 and ACTH levels at this active dose.

6-(5-Cyclopropylcarbamoyl-3-fluoro-2-methyl-phenyl)-N-(2,2-dimethylpropyl)-nicotinamide can therefore normalise sickness like behaviours by normalising cytokine levels and HPA axis function.

Study 2

A clinical trial to assess 6-(5-Cyclopropylcarbamoyl-3-fluoro-2-methyl-phenyl)-N-(2,2-dimethylpropyl)-nicotinamide for use in depression will typically be a randomised, double-blind, parallel-group with dosing of the active agent at a suitably acceptable dose against a placebo.

A second, higher dosage trial of the active agent can be initiated if a stronger cytokine level decrease is desired, and/or no-minimal clinical signal seen in the first dosing.

The duration of treatment should be approximately 6-weeks with visits: Weeks 0, 1, 2, 4, and 6. The patient population should be enriched at screening for symptoms of loss of energy & interest, fatigue, psychomotor retardation, and increased cytokine levels.

Follow up visits: 1 week after last dose (Week 7)
Sample size: approximately 30-40:20-30 (active:placebo)
Study assessment should be done using a Bayesian approach.

One desired primary outcome is to assess if treatment with 6-(5-Cyclopropylcarbamoyl-3-fluoro-2-methyl-phenyl)-N-(2,2-dimethylpropyl)-nicotinamide will reduce cytokine levels in the patient during a Major Depressive Episode. The desired secondary outcome is to evaluate the relationship between plasma cytokine levels, efficacy endpoints and drug exposure on: Depression symptoms (HAM-D Bech, IDS-C and QIDS-SR); Psychomotor retardation (Digit Symbol Test, item analysis from scales); Fatigue (FACIT-F1) and on Sleep parameters (scores from scales plus LSEQ).

All publications, including but not limited to patents and patent applications, cited in this specification are herein incorporated by reference as if each individual publication were specifically and individually indicated to be incorporated by reference herein as though fully set forth.

The invention claimed is:

1. A method for treating one or more psychiatric disorder selected from the group consisting of depression, schizophrenia, anxiety and a sleep disorder in a human in need thereof which comprises administering to said human, an effective amount of the compound 6-(5-Cyclopropylcarbamoyl-3-fluoro-2-methyl-phenyl)-N-(2,2-dimethylpropyl)-nicotinamide or a pharmaceutically acceptable salt.

2. The method according to claim 1 wherein the compound is 6-(5-Cyclopropylcarbamoyl-3-fluoro-2-methyl-phenyl)-N-(2,2-dimethylpropyl)-nicotinamide.

3. The method according to claim 1 wherein the psychiatric disorder is depression.

4. The method according to claim 1 wherein the psychiatric disorder is schizophrenia.

5. The method according to claim 1 wherein the psychiatric disorder is anxiety.

6. The method according to claim 1 wherein the psychiatric disorder is a sleep disorder.

* * * * *